United States Patent [19]

Noll et al.

[11] 4,230,001
[45] Oct. 28, 1980

[54] TATOOING PINCERS FOR MARKING EARS OF ANIMALS

[76] Inventors: Erwin Noll, Klein-Weinbach 1; Karlheinz Knoerr, Fichtenhof, both of 6294 Weinbach 4, Fed. Rep. of Germany

[21] Appl. No.: 42,882

[22] Filed: May 29, 1979

[51] Int. Cl.³ .............................................. B43K 5/00
[52] U.S. Cl. ................................................... 81/9.22
[58] Field of Search ......................... 30/358, 366, 367; 81/9.22

[56] References Cited

U.S. PATENT DOCUMENTS 2,359,699   10/1944   Valentine ........................... 30/367 X

FOREIGN PATENT DOCUMENTS 110725   3/1900   Fed. Rep. of Germany ............ 81/9.22
2814987   5/1979   Fed. Rep. of Germany ............ 81/9.22

Primary Examiner—James G. Smith
Attorney, Agent, or Firm—Remy J. VanOphem

[57] ABSTRACT

Tatooing pincers for marking ears of animals by injection of tatooing liquid. Pincers comprise a support and first and second jaws. Second jaw carries a number of hollow needles protruding to first jaw. Second jaw is yieldably connected to a drive by an intermediate part comprising a pump chamber connected with the hollow needles. The volume of the pump chamber is reduced when intermediate part yields under increased pressure after needles have fully penetrated animals ear between jaws, and tatooing liquid in pump chamber is injected via needles. Thus increased pressure provides for cleaning of needle holes from particles of skin resulting from penetration. Tatooing liquid is sucked into pump chamber from a storage chamber via check valves. A pneumatic drive may be used to facilitate operation.

10 Claims, 1 Drawing Figure

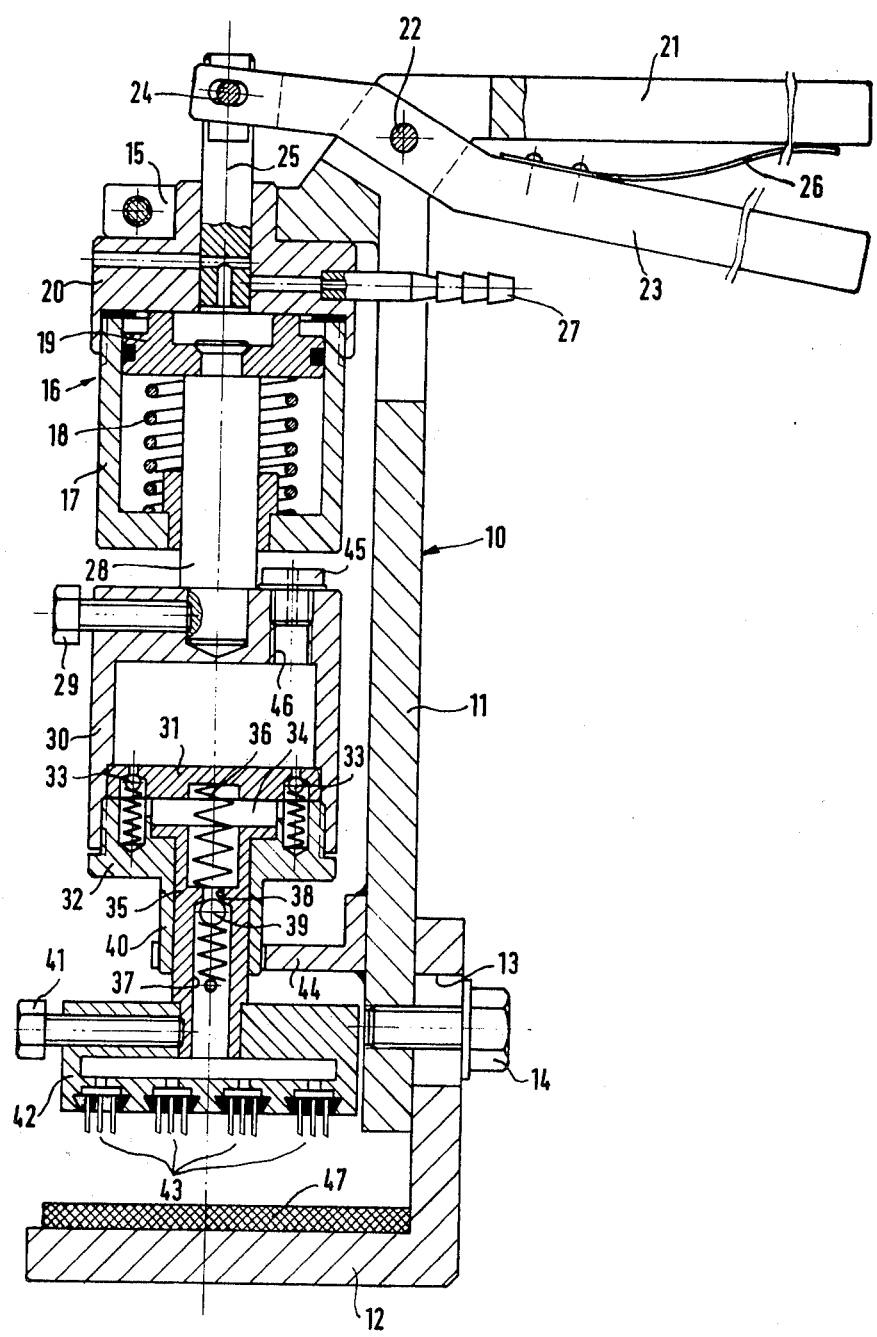

TATOOING PINCERS FOR MARKING EARS OF ANIMALS

FIELD OF THE INVENTION

The invention relates to improved tatooing pincers for marking ears of animals by injection of tatooing liquid.

BACKGROUND OF THE INVENTION

Tatooing pincers preferably may be utilized in farms for breeding of cattle, pigs, sheeps and other animals for which marking is wanted particularly under special rules of Government.

Usual pincers for this purpose have solid needles by which the ears of the animals to be tatooed are only pricked, and the tatooing liquid is applied to the pricked ears by a special operation which is manually carried out. Tatooing in this way is complicated because an additional person is needed for holding fast the nervous animal after pricking.

German Pat. No. 8 6515 (Daws) shows and describes tatooing pincers having hollow needles through which tatooing liquid is injected from a pump chamber when pincers open under the force of an opening spring. During pricking, i.e. during closing of pincers, pump chamber is sucking tatooing liquid from a storage chamber via at least one check valve. When the hollow needles penetrate the skin of the ear to be tatooed particles of skin may enter into the needle holes clogging them. When the pincers open, the force of the opening spring is too small for cleaning the needle holes so that marking may be incomplete. Thus such pincers have not been reduced to practice.

Therefore, it is an object of the invention to provide pincers for marking ears of animals by injecting tatooing liquid into the ears of animals through hollow needles, said pincers avoiding the risk of uncomplete marking.

It is another object of the invention to provide tatooing pincers for marking the ears of animals by injecting tatooing liquid through hollow needles in which clogging by particles of animals skin is effectively avoided.

It is still another object of the invention to provide tatooing pincers for marking of the ears of animals by injecting tatooing liquid through hollow needles whereat increased pressure after the needles have penetrated animal's ear is used for the injection of tatooing liquid.

Still another object of the invention is to provide tatooing pincers for marking ears of animals by injecting tatooing liquid through hollow needles, said pincers being adjustable for different thickness of the ears to be tatooed.

Still a further object of the invention is to provide tatooing pincers for marking ears of animals by injecting tatooing liquid through hollow needles which pincers may be easily used by one person only.

SUMMARY OF THE INVENTION

In accordance with the invention, tatooing pincers for marking ears of animals by injection of a tatooing liquid are provided which overcome the problems associated with said tatooing pincers of the prior art. The tatooing pincers according to the invention comprise a portable support structure carrying a first jaw thereon. A second jaw is movably arranged in direction to the first jaw and has a cavity therein. A number of hollow needles are carried by said second jaw and protrudes against said first jaw, said hollow needles being connected with said cavity. A drive means is arranged on said support structure for moving said second jaw in direction of said first jaw. An intermediate means are operatively connected between said drive means and said second jaw in a yielding relationship. Said intermediate means yield under increased pressure after said needles have fully penetrated an animal's ear located between said first and second jaws. Further a storage chamber for tatooing liquid and a pump chamber are provided on said tatooing pincers. The pump chamber is comprised by said intermediate means and is connected to said storage chamber at said cavity by check valves. The volume of the pump chamber is reduced when said intermediate means yields thereby tatooing liquid is pressed out through said pump chamber, said cavity and said hollow needles into the animal's ear.

Yielding of said intermediate means will begin as soon as said second jaw rests against the animal's ear thus increasing the resistance for operating the pincers. It is apparent that also the pressure in the pump chamber will be increased from this instant onward and, therefore, impurities in the needle holes resulting from penetrated particles of skin will be effectively pressed out of the needle holes so that correct and complete tatooing is guaranteed.

To further guarantee good visibility of the marking on the surface of the ear, in accordance with a preferred embodiment of the invention, the length of protrusion of said needles is substantially less than the thickness of the ear located between the first and second jaws. Also said first jaw preferably is adjustably mounted on said support structure for adjustment of the distance between the first and second jaws. On this way the yielding and thus the amount of liquid injected into the ear may be correctly adapted to the required visibility.

In accordance with another preferred embodiment, the pump chamber is formed by a pump cylinder and a pump piston slidably arranged in said pump cylinder, whereat said pump cylinder is connected with said drive means and said pump piston is carrying said second jaw. Preferably a spring means is arranged in said pump cylinder between said pump cylinder and said pump piston, and said spring means yields under increased pressure after said needles have fully penetrated the ear located between the first and second jaws. Said storage member may be comprised by said intermediate means adjacent said pump chamber, and a wall separating said chambers may be provided with at least one check valve.

The tatooing pincers according to the invention allows succeeding tatooing of any number of animals without interruption which, however, may result in early fatigue of the operator because considerable energy will be required for pressing the liquid through the capillary holes in the needles. Therefore, according to a special embodiment of the invention, the drive means preferably is a pneumatic drive, and a control means is provided for manually controlling said pneumatic drive which may be supplied by a compressed air source available in most agricultural plants.

In order to replenish the storage chamber and also in order to facilitate change of the needle pattern, according to still another preferred embodiment of the invention, said second jaw and said intermediate means are combined to a unit which is detachably carried by said pneumatic drive.

Other features and advantages of the invention will be set forth in, or apparent from, the detailed description of the preferred embodiment shown in the drawing which is a longitudinal section through pincers according to the invention.

BRIEF DESCRIPTION OF THE DRAWINGS

FIG. 1 shows a longitudinal cross section of the device.

DESCRIPTION OF THE PREFERRED EMBODIMENT

Referring to the drawing, the tatooing pincers shown include a three-armed support structure 10. A counter jaw 12 has a slotted hole 13 for adjustably mounting it on the first arm 11 of support structure 10 by means of the screw 14. A second arm 15 of support structure 10 is adapted to support a pneumatic drive 16 comprising an air cylinder 17, in which a piston 19 is slidable against a reset spring 18 and further comprising a valve housing 20. The third arm 21 of support structure 10 provides a handle cooperating with a second handle 23 pivotally connected to support structure 10 for manipulating and actuating the pincers. For this purpose second handle 23 is elongated beyond bolt 22 and pivotally connected to a shift valve 25 by means of a bolt 24. Central and transverse bores in shift valve 24 will vent the space on the upper side of piston 19 in cylinder 17 to atmosphere in one end position of shift valve 25 and connect said space in another end position, i.e. when handles 21, 23 are pressed together against the force of a leave spring 26, to a hose coupling 27 to which a hose may be connected for supplying compressed air from a pressure source to downwardly move piston 19 and piston rod 28 of piston 19 which protrudes out of cylinder 17.

A cup-shaped storage container 30 for storing tatooing liquid is detachably connected to the protruding end of the piston rod 28 by means of a fixing screw 29, and a valve plate 31 is sealingly mounted in storage container 30 by means of a cup cylinder 32 screwed into the internally threaded lower end of storage container 30.

Valve plate 31 has two diametrically opposed openings provided with check valves 33 providing connection from the storage chamber in the storage container 29 to a pump chamber 34 formed by the enlarged upper part of an axial bore through pump cylinder 32. A pump piston 35 having an enlarged upper end is slidably received in said axial bore and may be moved in an upward direction against the force of a pressure spring 36 until its upper end face rests on valve plate 31. Pump piston 35 has an axially through bore provided with a restriction 38 and a check valve 39 which allows flow of tatooing liquid only in downward direction.

Pump piston 35 slidably penetrates a collar shaped protrusion 40 on pump cylinder 32, and the lower end of pump piston 35 is detachably connected to a needle jaw 42 having a cavity therein which communicates with the through bore in pump piston 35. A number of hollow injection needles 43 in the pattern to be tatooed is arranged in the bottom wall of needle jaw 42 the holes in the needles being in communication with the cavity in needle jaw 42. The lower ends of the hollow needles are pointed similar to syringes the length of protrusion of hollow needles 43 being substantially less than the thickness of the ears to be tatooed.

Collar shaped protrusion 40 is slidably guided in a bifurcated bracket 44 secured on the first arm 11 of support structure 10. When fixing screw 29 is unscrewed bifurcated bracket 44 allows dismounting of storage container 30, pump cylinder 32 and needle jaw 42 as a unit for filling tatooing liquid into storage container 30 through a filling hole 46 which is normally closed by a venting screw 45.

Counter jaw 12 may be provided with an elastic layer 47 of plastic or similar material.

When the pincers described are to be used the operator firstly has to adjust the gap between the jaws 12, 42 to a distance allowing the entrance of the ears to be tatooed which may be made by loosening and tightening again fixing screw 14. Also hose coupling 27 has to be connected to a pressure source by means of a suitable hose. Hereafter pincers are ready for use.

For tatooing an animal the operator will grip the pincers on handles 21, 23 and embrace animal's ear between jaws 12, 42. By pressing handles 21, 23 together shift valve 25 will be moved down in the lower end position and compressed air may flow from the pressure source via hose coupling 27 and the bores in slide valve 25 to the upper surface of piston 29 to move piston 19 and piston rod 28 downwardly thereby compressing spring 18. Piston rod 28 drives storage container 30 and pump cylinder 32 also in downward direction and pump piston 35 and needle jaw 42 will follow because of the tensional connection provided by pressure spring 36. It is apparent that by this movement hollow needles 43 will penetrate into the skin and partly into the flesh of animal's ear until needle jaw 42 will rest against said skin of the ear. Pressure spring 36 is dimensioned to yield when this condition is reached which brings about that pump piston 35 moves in pump cylinder 32 upwardly and tatooing liquid present in pump chamber 34 will be pressed through restriction 38, bore 37, cavity in needle jaw 42 and needle holes into skin and flesh of animal's ear. Eventual impurities formed by particles of skin and flesh will be pressed out of needle holes because of the high pressure of tatooing liquid under this condition.

This injection mode will continue until pump piston 35 comes to a rest against valve plate 31 or piston 19 in air cylinder 17 has terminated its downward stroke. By suitably adjusting counter jaw 12 by means of fixing screw 14 the end of the downward stroke of piston 19 will be attained before pump piston 35 comes to rest against valve plate 31 which means that the animal's ear will not be impinged by the full force of the pressure drive.

As soon as pricking of needles 34 into the animal's ear and injecting tatooing liquid is terminated the operator will release handle 23 which will move shift valve 25 under the force of leave spring 26 upwardly which brings about that air cylinder 17 will be vented and piston 19 will return to the upper end position under the force of pressure spring 18. Piston rod 28 takes along also storage container 30 and pump cylinder 32 thereby allowing pressure spring 36 to relax and at least to pull hollow needles 43 out of animal's ear. During relaxing movement of pressure spring 36 the volume of pump chamber 34 increases and tatooing liquid is sucked out of the storage chamber in storage container 30 into pump chamber 34 via check valves 33 opening under this condition. The pincers is now ready for the next tatooing mode.

For purpose of change of the pattern to be tatooed needle jaw 42 may be dismounted by loosening of fixing screw 41, and the needle pattern may be changed or another needle jaw may be mounted on pump piston 35 by means of fixing screw 41.

What we claim is:

1. Tatooing pincers for marking ears of animals by injection of a tatooing liquid, said pincers comprising:
    a portable support structure,
    a first jaw carried by said support structure,
    a second jaw movably arranged in direction to said first jaw, said second jaw having a cavity therein,
    a number of hollow needles carried by said second jaw and protruding against said first jaw, said hollow needles being connected with said cavity,
    a drive means arranged on said support structure for moving said second jaw in direction to said first jaw,
    an intermediate means operatively connecting said drive means and said second jaw in a yielding relationship, said intermediate means yielding under increased pressure after said needles having fully penetrated an animal's ear located between said first and second jaws,
    a storage chamber for tatooing liquid and
    a pump chamber comprised by said intermediate means and connected to said storage chamber and said cavity by check valves,
    the volume of the pump chamber being reduced when said intermediate means yields thereby pressing tatooing liquid out of said pump chamber through said cavity and said hollow needles into animal's ear.

2. Tatooing pincers according to claim 1 wherein the length of protrusion of said needles is substantially less than the thickness of the ear located between said first and second jaws.

3. Tatooing pincers according to claim 1 wherein said first jaw is adjustably mounted on said support structure for adjustment of the distance between said first and second jaws.

4. Tatooing pincers according to claim 2 in which said first jaw is adjustably mounted on said support structure for adjustment of the distance between said first and second jaws.

5. Tatooing pincers according to claim 1 wherein said pump chamber is formed by a pump cylinder and a pump piston slidably arranged in said pump cylinder, said pump cylinder being connected with said drive means and said pump piston carrying said second jaw.

6. Tatooing pincers according to claim 5 wherein a spring means is arranged in said pump cylinder between said pump cylinder and said pump piston, said spring means yielding under increased pressure after said needles having fully penetrated the ear located between said first and second jaws.

7. Tatooing pincers according to claim 5 wherein said storage chamber is comprised by said intermediate means adjacent said pump chamber, a wall separating said chambers being provided with at least one check valve.

8. Tatooing pincers according to claim 6 wherein said storage chamber is comprised by said intermediate means adjacent said pump chamber, a wall separating said chambers being provided with at least one check valve.

9. Tatooing pincers according to claim 1 wherein said drive means is a pneumatic drive, a control means being provided for manually controlling said pneumatic drive.

10. Tatooing pincers according to claim 9 wherein said second jaw and said intermediate means are combined to a unit, said unit being detachably carried by said pneumatic drive.

* * * * *

UNITED STATES PATENT OFFICE
CERTIFICATE OF CORRECTION

Patent No. 4,230,001　　　　　　　　Dated October 28, 1980

Inventor(s) Erwin Noll and Karlheinz Knoerr

It is certified that error appears in the above-identified patent and that said Letters Patent are hereby corrected as shown below:

Column 1, line 38, delete the word "uncomplete" and insert ----incomplete----.

Column 2, line 5, delete the word "are" and insert ----is----.

Column 3, line 29, delete the numeral "24" and insert ----25----.

Column 4, line 53, delete the numeral "34" and insert ----43----.

Signed and Sealed this

Twenty-fourth Day of February 1981

[SEAL]

Attest:

Attesting Officer

RENE D. TEGTMEYER

Acting Commissioner of Patents and Trademarks